(12) United States Patent
Koppes et al.

(10) Patent No.: US 6,632,305 B2
(45) Date of Patent: *Oct. 14, 2003

(54) 1,2,4-TRIAZOLO[4,3-A][1,3,5]TRIAZINE-3,5,7-SUBSTITUTED PRECURSOR, AND PROCESS, AND COMPOUNDS THEREFROM

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/171,114

(22) Filed: Jun. 14, 2002

(65) Prior Publication Data

US 2003/0013878 A1 Jan. 16, 2003

Related U.S. Application Data

(63) Continuation-in-part of application No. 09/874,946, filed on Jun. 6, 2001, now Pat. No. 6,423,844.

(51) Int. Cl.[7] .................. C07D 487/14; C06B 45/10; C06C 15/00; A61K 31/53; A01N 43/713
(52) U.S. Cl. ................. 149/56; 149/76; 149/119; 504/232; 514/241; 514/185; 544/179; 544/196; 544/198; 544/204
(58) Field of Search ................ 544/184, 179; 514/241, 185; 504/232; 149/56, 76, 119

(56) References Cited

U.S. PATENT DOCUMENTS

| | | | |
|---|---|---|---|
| 2,473,797 A | 6/1949 | Kaiser et al. ............ 260/249.5 |
| 2,475,440 A | 7/1949 | Walter .................... 260/239 |
| 3,061,605 A | 10/1962 | D'Alelio ................. 260/239.7 |
| 3,939,084 A | 2/1976 | Sullivan .................. 252/47.5 |
| 4,517,182 A | 5/1985 | Chang .................... 514/413 |
| 4,549,018 A | 10/1985 | Siedle .................... 544/225 |
| 4,565,815 A | 1/1986 | Kim et al. ............... 514/246 |
| 4,656,171 A | 4/1987 | Austel et al. ............. 514/250 |
| 4,734,413 A | 3/1988 | Wade ..................... 514/222 |
| 4,954,498 A | 9/1990 | Mertens et al. ........... 514/254 |
| 5,173,492 A | 12/1992 | Suzuki et al. ............ 514/267 |
| 5,246,932 A | 9/1993 | Caulkett et al. .......... 514/245 |
| 5,260,291 A | 11/1993 | Lunt et al. .............. 514/183 |
| 5,270,316 A | 12/1993 | Suzuki et al. ............ 514/267 |
| 5,281,706 A | 1/1994 | Coburn et al. ............ 544/179 |
| 5,677,309 A | 10/1997 | Chen et al. .............. 517/267 |
| 5,682,014 A | 10/1997 | Highsmith et al. ......... 149/36 |
| 5,789,407 A | 8/1998 | Suzuki et al. ............ 514/246 |
| 5,792,766 A | 8/1998 | Chen et al. .............. 514/243 |
| 5,869,659 A | 2/1999 | Stolle et al. ............ 544/114 |
| 5,917,146 A | 6/1999 | Hiskey et al. ............ 149/36 |
| 5,955,465 A | 9/1999 | Chen et al. .............. 514/267 |
| 6,060,478 A | 5/2000 | Gilligan et al. .......... 514/258 |
| 6,075,016 A | 6/2000 | Chasin et al. ............ 514/183 |
| 6,103,731 A | 8/2000 | Chen et al. .............. 514/267 |
| 6,214,139 B1 | 4/2001 | Hiskey et al. ............ 149/36 |
| 6,297,252 B1 | 10/2001 | Chen et al. .............. 514/267 |
| 6,312,537 B1 | 11/2001 | Hiskey et al. ............ 149/36 |
| 6,313,124 B1 | 11/2001 | He et al. ................ 514/246 |

OTHER PUBLICATIONS

Article: "The Synthesis and Dimeoth–Type Rearrangement of 5,7–Bis(dimethylamino)–3–(methylthio)–s–triazolo[4,3–a]–s–triazine", DeMilo et al., J. Heterocyclic Chem. 10, 231 (Apr. 1973), pp 231–233.

Article: "New Synthesis of Dyes of the Triazine", Series II. VAT Dyes of the Triazolo–Triazine Series by A. Titkov and I.D. Pletnev, Scientific Research Institute of Intermediates and Dyes, translated from Zhurnal Obshchel Khimil, vol. 33, No. 4, pp. 1355–1357, Apr. 1963.

Abstract: No. 93042a Basic azo dye. Maeda, Hhigeo et al. (40–Dyes, vol. 81, 1974), referencing Maeda et al. Japan Kokai 74 24,226.

Abstract: No. 122766x Basic azo dye. Maeda, Hhigeo et al. (40–Dyes, vol. 81, 1974), referencing Maeda et al. Japan Kokai 74 27,287.

Article: "Chemistry of Dicyandiamide V Structures of Guanazo– and Pyro–Guanazoles, and Reaction of Dicyandiamide with 3–Amino–5–Substituted–1,2,4,4H–Triazoles", kaiser et al. J. Organic Chemistry, vol. 18, 1953, pp. 1610–1614.

*Primary Examiner*—Richard L. Raymond
*Assistant Examiner*—Venkataraman Balasubramanian
(74) *Attorney, Agent, or Firm*—Mark Homer

(57) ABSTRACT

The present invention includes a precursor compound pertaining to a 1,2,4-Triazolo[4,3-a][1,3,5]Triazine compound, particularly a 1,2,4-Triazolo[4,3-a][1,3,5]Triazine-3,5,7-Triamine, and novel fused ring structures such as triazolyl-tetrazinyl-aminotriazine compounds, and complexes and salts thereof, and other such chemical structures.

20 Claims, No Drawings

1,2,4-TRIAZOLO[4,3-A][1,3,5]TRIAZINE-3,5,7-SUBSTITUTED PRECURSOR, AND PROCESS, AND COMPOUNDS THEREFROM

This application is a continuation-in-part (CIP) of U.S. patent application Ser. No. 09/874,946, entitled "Process for Making 1,2,4-Triazolo[4,3-a][1,3,5]Triazine-3,5,7-Triamine", filed Jun. 6, 2001 which is now U.S. Pat. No. 6,423,844.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel fused ring structures useful for providing a platform for novel explosive and pyrotechnic compounds, particularly high nitrogen content, low carbon content energetic compounds, dyes, pharmaceutical and other compositions. The present invention includes a precursor compound pertaining to a 1,2,4-Triazolo[4,3-a][1,3,5] Triazine compound, particularly a 1,2,4-Triazolo[4,3-a][1,3,5]Triazine-3,5,7-Triamine, and novel fused ring structures such as triazolyl-tetrazinyl-aminotriazine compounds, and complexes and salts thereof, and other such chemical structures as detailed herein.

2. Brief Description of the Related Art

Development of specialized chemical compounds requires proper precursor chemical structures.

Current methods that purport to synthesize 1,2,4-triazolo[4,3-a][1,3,5]triazine-3,5,7-triamine all involve heating dicyandiamide and hydrazine dihydrochloride at elevated temperatures (100° C. or higher) for significant amounts of time in order to condense the dicyandiamide. This method was described by Kaiser et al. in a paper published in the Journal of Organic Chemistry, Vol. 18, 1953, page 1610.

Using this synthesis method theoretically provides for two possible isomeric structures of triazolotriazinetriamine (see I and II below). The first structure is the [4,3-a] triazolotriazinetriamine, pictured below as I. The second structure is the [1,5-a]triazolotriazinetriamine, pictured below as II. The product by Kaiser et al., resulting from the method above, was assigned the structure of I based upon degradation/oxidation studies of the product. However, these types of studies provide for a large degree of uncertainty as to structure.

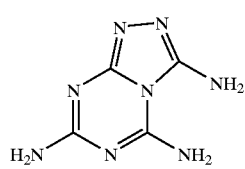

I

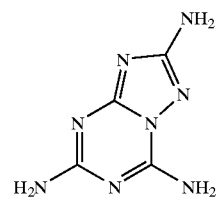

II

Recently, product derived from the above process was tested using X-ray diffraction, an extremely reliable technique, and, rather than the expected product I as originally reported, it was found that the actual structure of the product was that of II. The commercial product based upon the above method, sold under the names 3,5,7-triamino-s-triazolo[4,3-a]-s-triazine or 3,5,7-triamino-1,2,4-triazolo[4,3-a]-1,3,5-triazine, has also been tested via X-ray diffraction and found to be the structure of II. Because of the above error, prior to the present invention, there is, therefore, no known process of synthesizing product I. Additionally, patents such as U.S. Pat. No. 3,939,084 to Sullivan purport to use a 3,5,7-Triamino-s-trizazolo (4,3-a)-s-triazine, as well as articles such as "New Synthesis of Dyes of the Triazine", Series II. VAT Dyes of the Triazolo-Triazine Series by A. Titkov and I. D. Pletnev, Scientific Research Institute of Intermediates and Dyes, translated from Zhumal Obshchel Khimil, Vol. 33, No. 4, pp. 1355–1357, April 1963 (see also Maeda et al. Japan Kokai 74 24,226 and 74 27,287), which are apparent mislabelings of the 3,5,7-Triamino-s-trizazolo (1,5-a)-s-triazine.

The effects of the structural difference between these two products on the chemical and physical properties are of interest in any application of monotriazolotriazine ring systems. Of particular interest for energetic uses of these products would be the energy release in detonation, which correlates to the density of the materials. An analysis of densities and potential energy releases of the products reveals that the product I has a higher potential energy release value than product II that is significant in defense related energetic systems. The product II has also been investigated for use in the dye industry as a chromophore coupled to anthraquinones and indoles, and, therefore, product I should have similar potential uses. Other aromatic structure systems also are of interest.

Due to the discovery that the chemical sold as product I is actually product II, and the chemical and physical properties of the two products are significant for many uses, it would be desirable to derive product I, and like compounds, provide for synthesis such compounds, as well as developing compounds from processes using product I and like compounds as a precursor.

SUMMARY OF THE INVENTION

The present invention includes a novel compound structure having the formula:

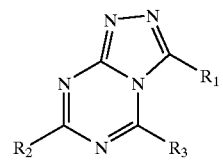

wherein $R_1$ is —$NH_2$, and $R_2$ and $R_3$ are independently electron donating groups, preferably where $R_1$, $R_2$ and $R_3$ are —$NH_2$.

The present invention further includes a novel fused ring structure having the formula:

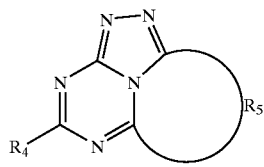

wherein $R_4$ is a substituent being or replacing the —$NH_2$ of the precursor, preferably being an electron donating group, and more preferably being —$NH_2$, and $R_5$ is a ring having greater than five atoms within the ring, preferably where $R_4$ is —$NH_2$ and $R_5$ forms a six-member or seven-member ring, more preferably with such ring having three or more nitrogen atoms. The ring may include substituents thereon.

The present invention also includes a pyrotechnic composition comprising a compound having the chemical structure:

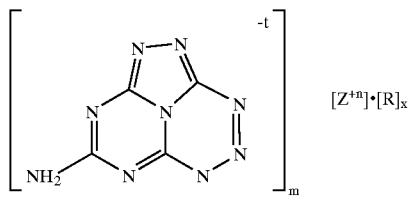

wherein $Z^+$ comprises $H^+$ or a cation; R comprises a complexing component; and, wherein m=1, 2 or 3; n=0, 1, 2 or 3; x=0, 1, 2 or 3; and t=0 or 1. The structure provides the complex and salt forms of triazolyl-tetrazinyl-aminotriazine. The present invention further includes a method of making a pyrotechnic composition comprising a triazolyl-tetrazinyl-aminotriazine compound comprising the steps of providing a triazolyl-triaminotriazine precursor and diazotizing the precursor to form the triazolyl-tetrazinyl-aminotriazine, or derivative thereof. Additionally, the present invention further includes a pyrotechnic composition comprising a triazolyl-tetrazinyl-aminotriazine compound.

The present; invention further includes a dye comprising a formula of:

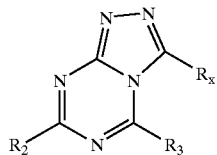

wherein $R_2$ and $R_3$ independently comprise electron donating groups, and Rx comprises an elongated conjugation sufficient to create a chromogen, with Rx preferably a chromophore, including azo dyes, having a (—N=N—) linkage or imino dyes having a (—N=$CR_aR_b$—) linkage, such as (—N=$CR_aA_x$—), where $R_a$ and $R_b$ represent additional dye forming substituents, such as aryl groups, e.g., multiple and/or fused aryl groups ($Ar_x$).

Preferably the dye comprises the formula of:

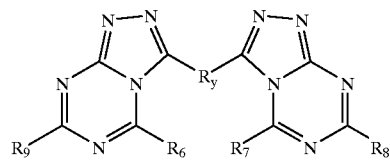

wherein $R_9$, $R_6$, $R_7$, and $R_8$ are electron donating groups, more preferably with $R_6$ and $R_7$ being —$NH_2$, and most preferably with $R_9$, $R_6$, $R_7$, and $R_8$ being —$NH_2$; and $R_y$ is —N=N—.

DETAILED DESCRIPTION OF THE INVENTION

The present invention includes a process for making a 1,2,4-triazolo[4,3-a][1,3,5]triazine-3,5,7-substituted compound, acid salt, particularly 1,2,4-triazolo[4,3-a][1,3,5]triazine-3,5,7-triamine, acid salt and a process for neutralizing the acid salt to make a 1,2,4-triazolo[4,3-a][1,3,5]triazine-3,5,7-substituted compound, particularly 1,2,4-triazolo[4,3-a][1,3,5]triazine-3,5,7-triamine, as well as the product of this process (the 1,2,4-triazolo[4,3-a][1,3,5]triazine-3,5,7-substituted compound, including the 1,2,4-triazolo[4,3-a][1,3,5]triazine-3,5,7-triamine is referred to herein as the "precursor"). Because of the reactive properties of the precursor, this precursor is useful in deriving compounds for ingredients in propellants, explosives, pyrotechnics, gas generators, ultraviolet absorbers, pharmaceuticals, colorants, etc. as later described.

The general process involves ring closure of a 2,4-substituted diamino-6-hydrazino-s-triazine with an acid and a chemical of the general formula RCN where the R comprises a leaving group, and then neutralizing said acid. Because the hydrazine nitrogen atoms that form the triazole ring are already in place on the 2,4-substituted-6-hydrazino-s-triazine, the final product formed is the desired [4,3-a] isomer, rather than the [1,5-a]isomer produced by the conventional dicyandiamide/hydrazine dihydrochloride methods. The general formulas for the process are set forth below:

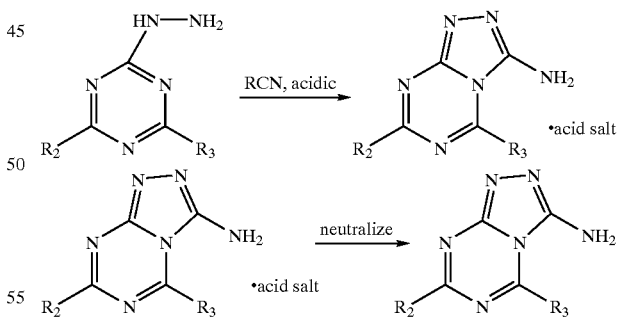

wherein the R comprises a leaving group, and $R_2$ and $R_3$ comprise electron donating groups.

More specifically, first, the invention comprises a process for the preparation of 1,2,4-triazolo[4,3-a][1,3,5]triazine-3,5,7-substituted compound, acid salt, with an amino group at the 3-position. In order to practice the present invention, one may first obtain or synthesize 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro- 1,3,5-triazine and hydrazine. A specific example is set forth in column 3, lines 60–70 of the above patent and are hereby incorporated by reference. While this particular method of synthesizing 2,4-diamino-6-hydrazino-s-triazine is specifically disclosed, any prior art method of synthesis would be appropriate to practice the present invention.

The first step in the present invention comprises dissolving the 2,4-diamino-6-hydrazino-s-triazine with an acid. This step is preferably carried out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid.

The second step comprises mixing the dissolved 2,4-diamino-6-hydrazino-s-triazine with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

The present invention also comprises a process to take the 1,2,4-triazolo[4,3-a][1,3,5]triazine-3,5,7-triamine, acid salt synthesized above, and neutralize the acid salt crystals in order to obtain a final product of 1,2,4-triazolo[4,3-a][1,3,5]triazine-3,5,7-triamine. This process involves the steps described above as well as the following steps.

First, the acid salt crystals are removed from the solution synthesized above. Then, the acid salt crystals are neutralized by mixing them with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

Due to the reactive nature of the —NH$_2$ from the five-member ring, derivatives of the precursor, particularly tricyclic fused compounds as described below, are useful in a wide range of fields, including for example, pharmaceuticals, including treating compositions, such as topical lotions including without limitation sunscreen, creams and/or therapeutic liquids, over-the-counter and/or prescription drugs, parental drugs, injectable drugs, food supplements, agricultural compositions, such as without limitation herbicides, pesticides, fungicides and/or fertilizers; ultraviolet (UV) stabilizers and ultraviolet absorbers, colorants such as dyes, pigments and other color applicants, such as without limitation paints, textile colorants and/or indicators, including liquid crystal uses and other indicators for computer display screens, explosives, pyrotechnics and gas generators, such as for use in airbags and other like functions; and/or fluids, such as functional fluids, additives and/or stabilizers, for use in machinery and/or other mechanical applications. The precursor may be used to anchor functional groups, such as benzophenones, benzotriazoles, substituted acrylonitriles and phenol-nickel complexes for ultraviolet absorbers, use of the precursor as an additive for a functional fluid (see e.g., U.S. Pat. No. 3,939,084 to Sullivan purporting to use a 3,5,7-Triamino-s-trizazolo (4,3-a)-s-triazine as an additive (col. 14, lns. 60–61) in Table I; which is a mislabeled 3,5,7-Triamino-s-trizazolo (1,5-a)-s-triazine), or chromogens as detailed below. For example, triazoles and/or triazines are known in the fields of agriculture (see e.g., U.S. Pat. No. 5,602,075 to Benko et al., herbicides), pharmaceuticals (see e.g., U.S. Pat. No. 5,380,714 to Jones et al., U.S. Pat. No. 5,457,091 to Jaehne et al., U.S. Pat. No. 5,246,932 to Caulkett et al., U.S. Pat. No. 6,107,300 to Bakthavatchalam et al. and U.S. Pat. No. 5,489,591 to Kobayashi et al.), colorants (see e.g., U.S. Pat. Nos. 3,758,309 and 3,725,067 to Bailey et al., U.S. Pat. No. 4,236,003 to Fletcher, and U.S. Pat. No. 4,621,046 to Sato et al.), and agricultural chemicals, medicines, dyes, paints, and the like, as various resin materials, such as aminoplast molded materials and flame retarding materials (see e.g., U.S. Pat. No. 6,127,538 to Tanaka et al.; see col. 1, lns. 26–30; see also U.S. Pat. No. 5,371,218 to Cipolli et al.).

The present invention further includes a novel fused ring structure having the formula:

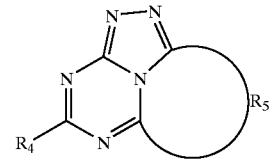

wherein R$_4$ is a substituent being or replacing the —NH$_2$ of the precursor, preferably being an electron donating group, and more preferably being —NH$_2$, and R$_5$ is a ring having greater than five atoms within the ring, preferably where R$_4$ is —NH$_2$ and R$_5$ forms a six-member or seven-member ring, more preferably with such ring having three or more nitrogen atoms. The ring may include substituents thereon.

As used herein, an "electron donating group" designates a group that will release or donate electrons more than hydrogen would if it occupied the same position in the molecule. See J. March, Advanced Organic Chemistry, 3$^{rd}$ Ed., John Wiley & Sons p. 238 (1985). These types of groups are well known in the art. Examples include lower alkylamino, diloweralkylamino, amino, halo, aryl, lower alkoxy, lower aralkoxy, aryloxy, mercapto, lower alkylthio, and the like, including for example, O$^-$, —COO$^-$, —OR$_\alpha$, —CR$_\alpha$R$_\beta$R$_\gamma$, —OCOR$_\alpha$, —NR$_\alpha$R$_\beta$, and SR$_\alpha$, where R$_\alpha$, R$_\beta$, and R$_\gamma$ groups are independently H or an alkyl group, such as methyl, ethyl, propyl, isopropyl, tert-butyl, isobutyl, and the like. The preferred electron donating groups are amino, hydroxy, lower alkoxy, lower alkylamino and diloweralkylamino. The most preferred electron donating group is amino. Lower used herein denotes straight-chain and branched hydrocarbon moieties containing from 1 to 8 carbon atoms. Electron donating groups include atoms that can stabilize the developing positive charge in a ring closure by Mesomeric Effect, such as methoxy groups.

The present invention includes novel triazolyl-tetrazinyl-aminotriazine compounds, and the complexes and salts thereof, that are particularly useful in energetic materials, such as explosive, pyrotechnic and/or gas generator compositions. These triazolyl-tetrazinyl-aminotriazine compounds have special applicability in demolitions, fireworks and airbag inflating compositions. For example, the fireworks compositions of the present invention are characterized as low-smoke compositions and can be formulated to be essentially smoke-free. Low smoke compositions have decreasing amounts of residual smoke after pyrotechnic burn that are operationally and commercially useful. The triazolyl-tetrazinyl-aminotriazine compounds, and their complexes and salts, provide a high-nitrogen content, low-carbon content-energetic material as a principal component within the pyrotechnic composition.

The present invention includes an energetic material, particularly a pyrotechnic composition, comprising a compound having the chemical structure:

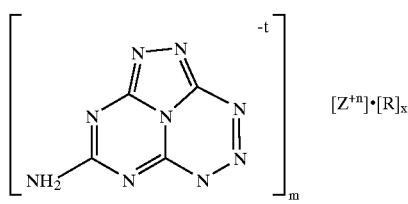

wherein $Z^+$ comprises $H^+$ or a cation; R comprises a complexing component; and, wherein m=1, 2 or 3; n=0, 1, 2 or 3; x=0, 1, 2 or 3; and t=0 or 1.

The complex form of the triazolyl-tetrazinyl-aminotriazine occurs when $Z^+$ comprises $H^+$, with H attached to a nitrogen of the compound, and the value of x is not 0. Complexes of the present invention include, for example, R=Dihydrazino-s-tetrazine, Trihydrazino-s-triazine, 5-Aminotetrazole, N-aminotriazoles, and bis-(1(2)H-tetrazol-5-yl)-amine.

The pyrotechnic compositions of the present invention further include metal and non-metal salts of the triazolyl-tetrazinyl-aminotriazine compound. In one particular embodiment, preferably m=n.

In addition to a complex or salt structure of the triazolyl-tetrazinyl-aminotriazine compound, a useful structure of the triazolyl-tetrazinyl-aminotriazine compound in pyrotechnic compositions includes $Z^+$ being $H^+$, t=1, m=1, n=1, and x=0. When $Z^+$ comprises $H^+$, and m and n are both equal to 1, the calculated heat of formation is approximately 255 kcal/mole (gas phase), and a density of approximately 1.77 g/cc (calcd) which provides significant energy to the pyrotechnic composition.

The $Z^+$ component of the triazolyl-tetrazinyl-aminotriazine compound preferably comprises a cation. As a salt, the compound may be selected from a large number and/or variety of cations as suitable for any particular pyrotechnic. Suitable cations of the present invention include those appropriate to provide color displays from combusting fireworks, particularly metals or amine salts. Metals of the present invention may include, without limitation sodium (Na), cobalt (Co), copper (Cu), aluminum (Al), nickel (Ni), barium (Ba), strontium (Sr), calcium (Ca), potassium (K), iron (Fe), titanium (Ti), magnesium (Mg), antimony (Sb) and the like. Additionally, typical amine salts may include compounds with $Z^+$ being, without limitation, $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, $C(NH_2)_3$, $(HONH_3)$, and bis(1(2)H-tetrazol-5-yl)-amine. $(C_2H_4N_9)$, the monohydrate of bis(1(2)H-tetrazol-5-yl)-amine $(C_2H_4N_9.H_2O)$. Ignition or combustion of $Z^+$ of the present invention preferably results in a color, however, additional salts and other compositions may be added in combination with the triazolyl-tetrazinyl-aminotriazine compounds to form the pyrotechnic compositions, as later described. Use of the metal salts of the triazolyl-tetrazinyl-aminotriazine compounds as colorants within the pyrotechnic compositions may generally include the metals conventionally used in pyrotechnic compositions. For example, strontium, barium, copper, and iron salts of triazolo-tetrazino-aminotriazine compounds, and salts thereof, can be expected to yield red, blue, green, yellow, purple, red-purple, and blue-green colorants.

The following structures exemplify non-limiting examples of possible salts for use in the pyrotechnic compositions of the present invention:

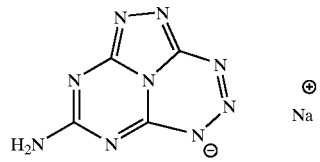

Examples 2 and 3

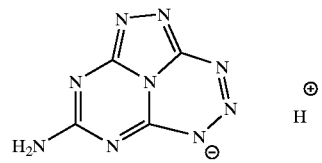

Example 4

Example 5

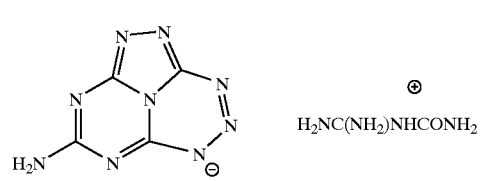

Example 6

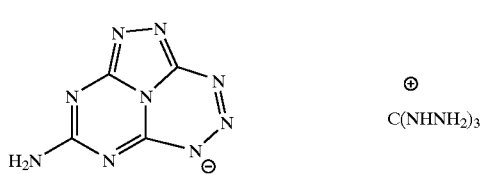

Example 7

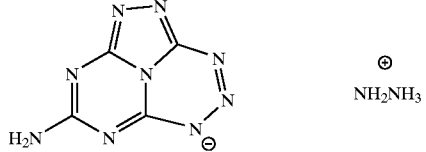

Example 8

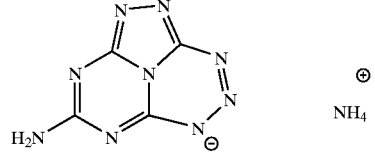

-continued

Example 9

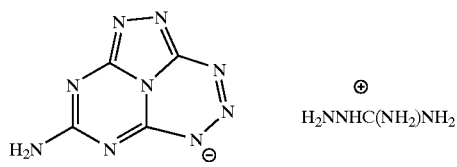
H₂NNHC(NH₂)NH₂

Example 10

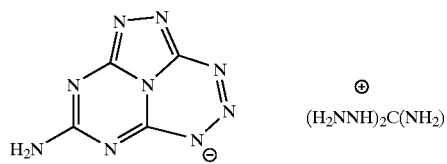
(H₂NNH)₂C(NH₂)

Example 11

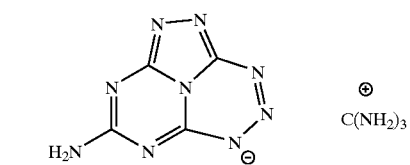
C(NH₂)₃

Example 12

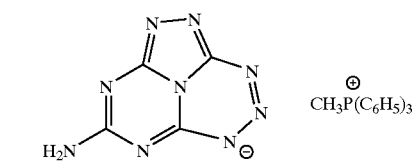
CH₃P(C₆H₅)₃

Example 13

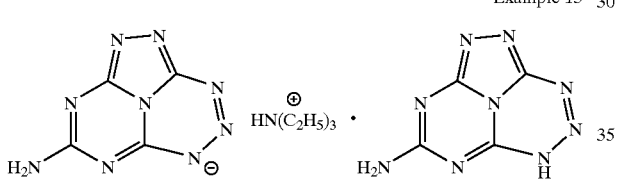
HN(C₂H₅)₃ ·

Example 14

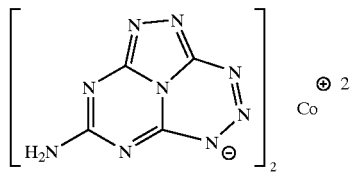
Co

Example 15

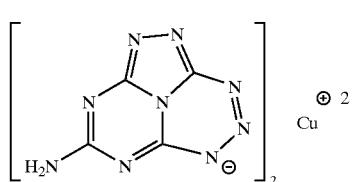
Cu

Example 16

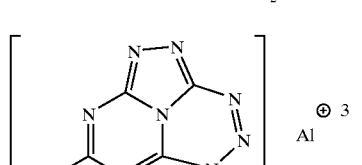
Al

Example 17

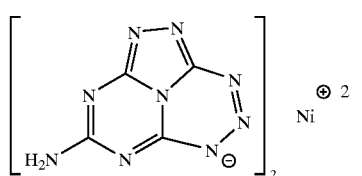
Ni

-continued

Example 18

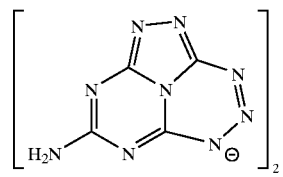
Ba

Example 20

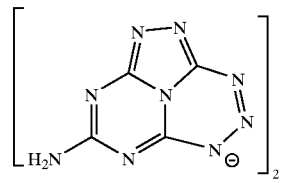
Mg

Example 19A

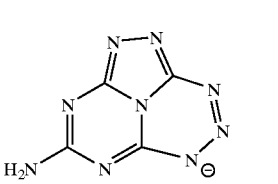
H₂NNH(C₂N₄)NHNH₃

Example 19B

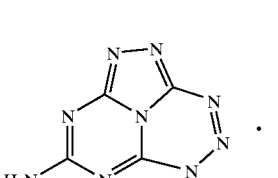
· H₂NNH(C₂N₄)NHNH₂

Example 21

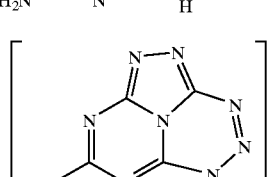
Sr

Example 22

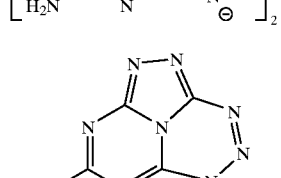
K

The pyrotechnic composition generally includes the addition of an oxidant to fully consume the carbon and hydrogen components of the pyrotechnic compositions during burning. Suitable oxidizers can generally include, without limitation, one or more alkaline earth metal nitrates, alkaline earth metal nitrites, alkali metal nitrates, alkali metal nitrites, transition metal oxides, such as ammonium perchlorate, alkali perchlorates such as potassium perchlorate and the like, ammonium nitrate, and alkali nitrates such as potassium nitrate and the like, or combinations thereof. Examples of the oxidizer include at least one of an alkali metal or an alkaline earth metal nitrate, a complex salt nitrate, such as $Ce(NH_4)_2 (NO_3)_6$ or $ZrO(NO_3)_2$, a dried, hydrated nitrate, such as $Ca(NO_3)_2 \cdot 4H_2O$ or $Cu(NO_3)_2 \cdot 2.5H_2O$, silver nitrate, an alkali or alkaline earth metal chlorate or perchlorate, ammonium perchlorate, a nitrite of sodium, potassium, or silver. Additionally, organic compositions such as a solid organic nitrate, nitrite, or amine, such as guanidine nitrate, nitroguanidine and 5-aminotetrazole may be included. The oxidizer may include silver nitrate or a co-melt or mixture comprising silver nitrate and at least one of an alkali metal nitrate, an alkaline earth metal nitrate, a complex salt nitrate, a dried, hydrated nitrate, an alkali metal chlorate, an alkali metal perchlorate, an alkaline earth metal chlorate, an alkaline earth metal perchlorate, ammonium perchlorate, sodium nitrite, potassium nitrite, silver nitrite, or a complex salt nitrite; and independently a solid organic nitrate, a solid organic nitrite, or a solid organic amine. Alkali chlorates are generally not preferred as oxidizer due to sensitivity concerns. Ammonium perchlorate and ammonium nitrate are preferred oxidizers as the absence of any metal ions is better for control of the fireworks color and eliminates any ash residue. Ammonium perchlorate is particularly preferred as the oxidizer to provide a source of chlorine ions to the pyrotechnic composition. Chlorine ion may be supplied by addition of a metal chloride salt as the colorant or by use of ammonium perchlorate as the oxidizer, or a part thereof. Ammonium nitrate is hygroscopic and compositions including ammonium nitrate must be protected from moisture.

The oxidizer is generally added with the triazolyl-tetrazinyl-aminotriazine compounds, or their complexes or salts, in amounts sufficient to provide about three equivalents of free oxygen. For example, the ammonium perchlorate oxidizes the triazolyl-tetrazinyl-aminotriazine anion to carbon dioxide and water if in a ratio of two parts by weight ammonium perchlorate to one part of the organic anion. The same degree of oxidation requires four parts ammonium nitrate. Generally, the compositions can include from about 30 percent by weight to about 60 percent by weight of the high-nitrogen content, low-carbon content energetic material, more preferably from about 35 percent by weight to about 55 percent by weight, together with about 40 to about 60 percent by weight of the selected oxidizer.

As previously described, the pyrotechnic may further include a colorant in addition to the triazolyl-tetrazinyl-aminotriazine complex or salt. Colorants may be additional metal salts, or other compositions, as known in the art. For example, each metal salt has an anticipated colorant effect within a pyrotechnic composition, as each metal has well-known spectra associated with the burning of that metal. These include strontium salts such as strontium nitrate ($Sr(NO_3)_2$) or strontium carbonate ($SrCO_3$) for the color red, calcium salts such as calcium carbonate for the color red-orange, barium salts such as barium nitrate ($Ba(NO_3)_2$), barium chlorate ($Ba(ClO_3)_2$) or boron compounds for the color green, sodium salts such as sodium nitrate for the color orange-yellow, or sodium oxalate ($Na_2C_2O_4$) or cryolite ($3NaF.AlF_3$) for yellow, copper salts such as copper oxide, $CUCO_3$, Paris Green [$CuAs_2O_4.Cu(Ac)_2$] for the color blue, potassium salts such as potassium chloride for the color purple or violet, and magnesium, aluminum, antimony salts such as antimony sulfide ($Sb_2S_3$) for the color white. Combinations of these and other metal salts may be used to provide additional colors, such as orange from a combination of calcium carbonate and sodium nitrate, red-purple from a combination of copper sulfide and strontium nitrate, and yellow from a combination of barium nitrate and sodium nitrate. Other metal salts such as cadmium, uranium, gold, mercury, arsenic, iron and lead may be used to provide other colors if desired, although many such salts are not generally preferred due to toxicity. Nitrate salts are generally more preferred than chloride salts as chloride salts tend to occur as hydrates and thus contribute undesired water. The colorant is generally added in amounts from about 0.5 percent by weight to about 20 percent by weight, preferably from about 1 percent by weight to about 10 percent by weight based on the total weight of fuel, oxidant and colorant. These additional salts may include metal salts of calcium, titanium, aluminum, magnesium, and the like. Metal flakes or particles may be added to the pyrotechnic compositions to provide a glitter effect. Suitable metals can include aluminum, magnesium, titanium and iron. Iron can generally be added in the form of steel shavings to avoid rusting problems from moisture.

One preferred pyrotechnic formulation includes a triazolyl-tetrazinyl-aminotriazine compound together with two parts ammonium perchlorate as the oxidizer for complete oxidation, with from about 10 percent by weight of a colorant. It is most preferred that the triazolyl-tetrazinyl-aminotriazine compound comprises a salt of cobalt or copper.

The pyrotechnic composition is formed from mixing or packing the triazolyl-tetrazinyl-aminotriazine compound, including its salt or complex, in an appropriate delivery combination for use as fireworks, with the appropriate mixing and packing being within the level of skill of a person of ordinary skill in the art of fireworks. The triazolyl-tetrazinyl-aminotriazine compound is diazotized from the triazolyl-triaminotriazine precursor, as taught herein, to form the appropriate pyrotechnic salt. Diazotization occurs by reacting the triazolyl-triaminotriazine precursor with a diazotization agent, for example nitrite salts, organic nitrites, and the like, such as, without limitation, nitric oxide, sodium nitrite, potassium nitrite and the like, with diazotizing agent known to those skilled in the art. The triazolyl-triaminotriazine precursor(s), including the acid salts thereof, are diazotized in an appropriate aqueous acid, such as for example hydrochloric or sulfuric acid, with the nitrite salt to give the ring-closed tetrazine product of the triazolyl-tetrazinyl-aminotriazine compound. The use of sodium nitrite (Z=Na) to form the triazolyl-tetrazinyl-aminotriazine compound is preferred. This reaction is represented below and in Examples 2 and 3. The triazolyl-tetrazinyl-aminotriazine compound (Z=Na) can be acidified to produce the parent acid of the triazolyl-tetrazinyl-aminotriazine compound (i.e., Z=H). Other triazolyl-tetrazinyl-aminotriazine compounds may be formed by neutralization of the parent acid or by cation exchange reactions with the sodium salt.

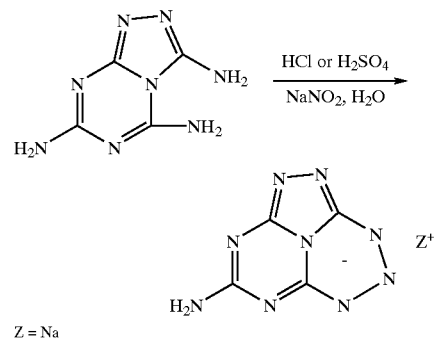

Z = Na

The preparation of triazolyl-tetrazinyl-aminotriazine salts by neutralization of the parent acid (Method A) occurs by reaction with amine bases or by reaction with metal hydroxides.

Cation exchange with the sodium salt to form the triazolyl-tetrazinyl-aminotriazine salts (Method B) occurs by the process that includes an aqueous solution of the sodium salt being mixed with a solution of barium nitrate, strontium nitrate, calcium nitrate, or other.

The present invention further includes a chromogen for providing a colorant of a dye or pigment comprising a formula of:

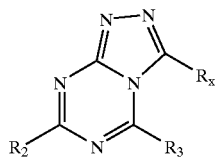

wherein $R_2$ and $R_3$ independently comprise electron donating groups, and Rx comprises an elongated conjugation sufficient to create a chromogen, with Rx preferably a chromophore, including azo dyes, having a (—N=N—) linkage or imino dyes having a (—N=$CR_aR_b$—) linkage, such as (—N=$CR_aAr_x$—), where $R_a$ and $R_b$ represent additional dye forming substituents, such as aryl groups, e.g., multiple and/or fused aryl groups ($Ar_x$). Representative units within the Rx group include anthraquinones, triphenylmethanes, azines, phthalocyanines, indoles, and the like.

In addition to the oxidative coupling reaction exemplified in Example 23 (Methods C and D), dyes may theoretically be formed by diazotization of the amino group on the triazole ring of an aminotriazolotriazine to produce a diazonium salt and then coupling the diazonium salt with various aromatic compounds. Preferably, an appropriate blocking group will be used on the triazine ring to prevent cyclization to form a tetrazine ring as occurs when the diazotization is performed on the [4,3-a]-triaminotriazolotriazine precursor. An example of a blocking group would be the methoxy group.

Preferably the dye comprises the formula:

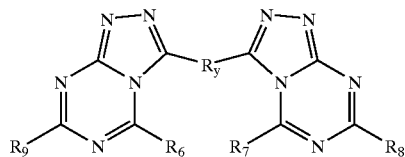

wherein $R_9$, $R_6$, $R_7$, and $R_9$ are electron donating groups, more preferably with $R_6$ and $R_7$ being —$NH_2$, and most preferably with $R_9$, $R_6$, $R_7$, and $R_8$ are —$NH_2$; and $R_y$ is —N—.

Precursor

The precursor comprises a 1,2,4-triazolo[4,3-a][1,3,5]triazine-3,5,7-triamine, acid salt or its neutralized form of 1,2,4-triazolo[4,3-a][1,3,5]triazine-3,5,7-triamine. The general process involves ring closure of 2,4-diamino-6-hydrazino-s-triazine with an acid and a chemical of the general formula RCN where the R comprises a leaving group, and then neutralizing the acid.

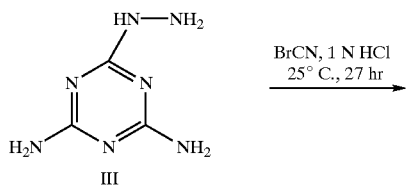

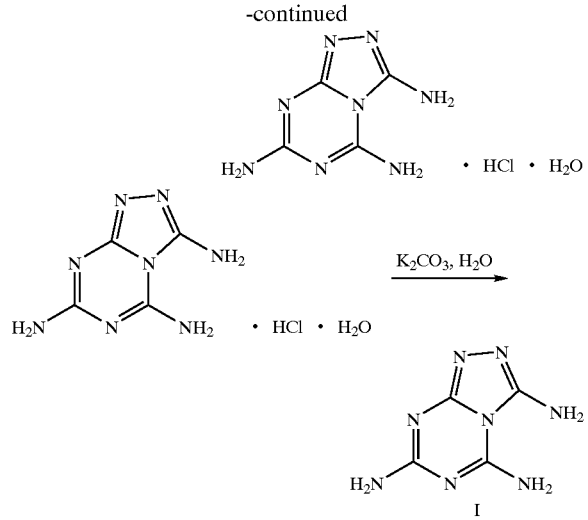

The structure of the precursor is shown below:

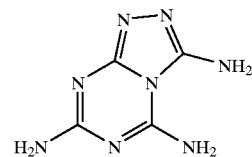

More specifically, the 1,2,4-triazolo[4,3-a][1,3,5]triazine-3,5,7-triamine, acid salt is derived first by obtaining or synthesizing 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent which is hereby incorporated by reference. While this particular method of synthesizing 2,4-diamino-6-hydrazino-s-triazine is specifically disclosed, any prior art method of synthesis would be appropriate to practice the present invention. The 2,4-diamino-6-hydrazino-s-triazine is -dissolved with an acid, preferably out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid. The dissolved 2,4-diamino-6-hydrazino-s-triazine is mixed with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

Neutralization of the 1,2,4-triazolo[4,3-a][1,3,5]triazine-3,5,7-triamine, acid salt crystals synthesized above to obtain a final product of 1,2,4-triazolo[4,3-a][1,3,5]triazine-3,5,7-triamine is accomplished by mixing the crystals with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The following examples (Examples 1A–1C) are preparations of the 1,2,4-triazolo[4,3-a][1,3,5]triazine-3,5,7-triamine precursors, with the chemical structures shown below:

EXAMPLE 1A

Preparation of 1,2,4-triazolo[4,3-a][1,3,5]triazine-3,5,7-triamine, hydrochloric salt hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962), which is incorporated herein by reference]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2×25 ml cold water. The crystals were air dried and then dried in a vacuum desiccator over Drierite to give 8.60 g (68.4% yield) of product. IR (KBr): 3300, 3155, 1708, 1695, 1624, 1534, 1490, 1444, 1339, 1173, 1073, 979, 845, 772 cm$^{-1}$. Anal. Calcd for $C_4H_6N_8$ (HCl) ($H_2O$): C, 21.77; H, 4.11; N, 50.79; Cl, 16.07. Found: C, 21.84; H, 4.25; N, 50.02; Cl, 16.02.

EXAMPLE 1B

Preparation of 1,2,4-triazolo[4,3-a][1,3,5]triazine-3,5,7-triamine

To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}C$ NMR ($CD_3CO_2D/D_2O$, 1:1 by vol): 145.7, 151.1, 151.9, 164.0. $^{13}C$ NMR ($D_2SO_4$): 133.6, 141.9, 143.1, 149.5. IR (KBr): 3413, 3314, 3096, 1654, 1611, 1540, 1480, 1430, 1375, 979, 859, 770 cm$^{-1}$. Anal. Calcd for $C_4H_6N_8$: C, 28.92; H, 3.64; N, 67.44. Found: C, 28.64; H, 3.65; N, 66.08.

EXAMPLE 1C

Preparation of 1,2,4-triazolo[4,3-a][1,3,5]triazine-3,5,7-triamine, hydrochloric salt hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

Examples 1A and 1C

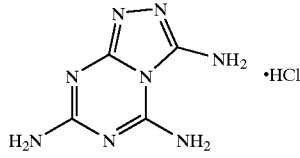

Example 1B

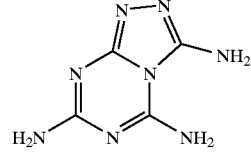

The following examples (Examples 2–18) are preparations of the triazolyl-tetrazinyl-aminotriazine compounds:

EXAMPLE 2

Preparation of triazolyl-tetrazinyl-aminotriazine, sodium salt (Z=Na)

1,2,4-triazolo[4,3-a][1,3,5]triazine-3,5,7-triamine, hydrochloric acid salt hydrate (4.20 g, 0.0190 mole) was added to aqueous hydrochloric acid stirred in an ice bath to produce a slurry [The aqueous hydrochloric acid was prepared by adding 8.0 g of 37% concentrated HCl (0.08 mole HCl) to 75 ml of water]. The ice-cold slurry was added in seven portions over approximately 15 minutes to a solution of 16.5 g (0.24 mole) of sodium nitrite in 50 ml of water stirred in an ice bath. Stirring in the ice bath was continued for two hours before the yellow mixture was allowed to warm to 20° C. over approximately one hour. The mixture was heated to 60° C. over 30 minutes and then held at 60–65° C. for one hour. The hot mixture was filtered to remove an insoluble brown solid, after which the filtrate was cooled to 5° C. to give 2.16 g of red crystals. Concentration of the aqueous mother liquor under reduced pressure gave an additional 0.73 g of product to bring the total yield to 2.89 g (70%), mp>300° C. (gradual decomp. with loss of red color above 220° C.). The product contains a small amount of a by-product (nitrotriazolo-diaminotriazine) which can be removed by filtration when the product is dissolved in warm water. Analysis showed: $^1H$ NMR (DMSO-$d_6$): 6.67 (s). $^{13}C$ NMR (DMSO-$d_6$): 146.1, 151.7, 153.1, 167.7. Anal. Calcd for $C_4H_2N_9Na$ ($H_2O$): C, 22.13; H, 1.86; N, 58.06, Na, 10.59. Found: C, 22.04; H, 1.93; N, 57.35, Na, 11.00.

EXAMPLE 3

Preparation of triazolyl-tetrazinyl-aminotriazine, sodium salt (from triazolo-triaminotriazole)

An ice cold slurry of 0.63 g (0.0038 mole) of 1,2,4-triazolo[4,3-a][1,3,5]triazine-3,5,7-triamine in 15 ml of aqueous sulfuric acid (containing 1.0 g, 0.01 mole $H_2SO_4$) was added in 1.5 ml portions over 5 minutes to a solution of 3.3 g (0.048 mole) of sodium nitrite in 10 ml of water stirred in an ice bath. The mixture was stirred at ice bath temperature for 2.5 hours before it was held at 20° C. for 10 minutes and then at 50–53° C. for 45 minutes. The warm mixture was filtered to remove an insoluble brown solid and the filtrate was held at 80–85° C. for 15 minutes. The red solution was allowed to stand at room temperature to precipitate red crystals (0.33 g). Concentration of the mother liquor gave additional product, raising the total to 0.43 g (52%).

EXAMPLE 4

Preparation of triazolyl-tetrazinyl-aminotriazine, (parent acid) (Z=H)

Triazolyl-tetrazinyl-aminotriazine, sodium salt hydrate (2.9 g, 0.0134 mole) was dissolved in 70 ml of warm water. The solution was stirred at 25° C. while adding dropwise 15 ml of 1N aqueous hydrochloric acid. The yellow precipitate that formed was removed by filtration and washed with cold water to give 1.9 g (81%) of yellow solid, mp 215° C., rapid dec. Analysis showed: $^1$H NMR (DMSO-$d_6$): 13.65 (very bs, 1H), 8.06, 7.96 (d, 2H). $^{13}$C NMR (DMSO-$d_6$): 143.9 (1C), 149.6 (2C), 167.5 (1C).

Examples 5 through 18 describe the preparation of additional salts of triazolyl-tetrazinyl-aminotriazine either by neutralization of the parent acid (Method A) or by cation exchange with the sodium salt (Method B).

EXAMPLE 5

Preparation of triazolyl-tetrazinyl-aminotriazine, guanyl urea salt (Z=$H_2$NC(NH$_2$)NHCONH$_2$) via neutralization of the parent acid (Method A)

A solution of 0.15 g (0.5 mmole) of N-guanyl urea sulfate hydrate, [$H_2$NC(NH$_2$)NHCONH$_2$]$_2$H$_2$SO$_4$ xH$_2$O, in 3 ml of water was neutralized with 1 ml of aqueous sodium hydroxide (containing 0.04 g, 1 mmole of NaOH). This solution (containing N-guanyl urea as a free base) was added dropwise to a stirred suspension of the parent acid (triazolo-tetrazino-aminotriazine) in 3 ml of water. The mixture was stirred for 2 hours at 25° C., then was cooled to 5° C., and the insoluble product was removed by filtration and washed with cold water to give 0.24 g (96%) of red solid, mp>300° C. (gradual decomp. with loss of red color above 240° C.). Analysis showed: $^1$H NMR (DMSO-$d_6$): 6.73 (s, 2H) 7.09 (bs, 2H), 8.04 (very bs, 4H). $^{13}$C NMR (DMSO-$d_6$): 146.1, 151.7, 153.1, 154.6, 155.2, 167.7. Anal. Calcd for $C_6H_9N_{13}O(H_2O)$: C, 24.24; H, 3.73; N, 61.26. Found: C, 24.19; H, 3.68; N, 60.71. X-ray crystal structure analysis also confirmed the structure of the product to be triazolyl-tetrazinyl-aminotriazine, guanyl urea salt hydrate.

EXAMPLE 6

Preparation of triazolyl-tetrazinyl-aminotriazine, triaminoguanidine salt [Z=C(NHNH$_2$)$_3$]via cation exchange (Method B)

A solution of triazolyl-tetrazinyl-aminotriazine, sodium salt hydrate (0.32 g, 1.45 mmole) in 10 ml of water was stirred at 25° C. while triaminoguanidinium nitrate (0.25 g, 1.50 mmole) was added in three portions over one minute. After a short time, red crystals began to precipitate from the solution. The mixture was stirred at 25° C. for two hours before it was cooled to 5° C. and filtered to give 0.25 g of red crystals. Additional product from concentration of the filtrate raised the total yield to 0.29 g (71%), mp 195° C., rapid dec. Recrystallization from water raised the mp to 203° C., rapid dec. Analysis showed: $^1$H NMR (DMSO-$d_6$): 4.48 (s, 6H), 6.65 (s, 2H), 8.59 (s, 3H). $^{13}$C NMR (DMSO-$d_6$): 146.1, 151.7, 153.1, 158.9, 167.7. Anal. Calcd for $C_5H_{11}N_{15}$ (H$_2$O): C, 20.07; H, 4.38; N, 70.21. Found: C, 20.22; H, 4.30; N, 69.64.

EXAMPLE 7

Preparation of triazolyl-tetrazinyl-aminotriazine, hydrazinium salt [Z=NH$_2$NH$_3$]

Via Method A: The parent acid was neutralized with one equivalent of aqueous hydrazine to give red crystals (74%), mp 200° C., rapid dec. Analysis showed: $^1$H NMR (DMSO-$d_6$): 6.68 (s) (merged with a broad s at 7.05). $^{13}$C NMR (DMSO-$d_6$): 146.1, 151.7, 153.1, 167.7. Anal. Calcd for $C_4H_7N_{11}$: C, 22.96; H, 3.38; N, 73.66. Found: C, 23.06; H, 3.51; N, 71.56.

EXAMPLE 8

Preparation of triazolyl-tetrazinyl-aminotriazine, ammonium salt [Z=NH$_4$]

Via Method A: The parent acid was neutralized in water with one equivalent of aqueous ammonia to give red crystals (74%), mp>300° C. (with gradual decomp and loss of red color above 220° C.). Analysis showed: $^1$H NMR (DMSO-$d_6$): 6.69 (s) 7.12 (bs). $^{13}$C NMR (DMSO-$d_6$): 146.1, 151.7, 153.1, 167.7. Anal. Calcd for $C_4H_6N_{10}$: C, 24.74; H, 3.12; N, 72.14. Found: C, 24.40; H, 3.04; N, 70.23.

EXAMPLE 9

Preparation of triazolyl-tetrazinyl-aminotriazine, aminoguanidinium salt [Z=$H_2$NNHC(NH$_2$)NH$_2$]

Via Method A: The parent acid was neutralized in water with aminoguanidine bicarbonate [$H_2$NNHC(=NH)NH$_2$ (H$_2$CO$_3$)]using equal molar amounts to give red crystals (81%), mp 227° C., dec. Analysis showed: $^1$H NMR (DMSO-$d_6$): 4.68 (s, 2H), 6.67 (s, 2H), 6.76, 7.23 (two bs, 4H), 8.58 (s, 1H). $^{13}$C NMR (DMSO-$d_6$): 146.1, 151.7, 153.1, 158.5, 167.7. Anal. Calcd for $C_5H_9N_{13}$: C, 23.90; H, 3.61;N, 72.48. Found: C, 23.65; H,3.65;N, 70.91.

EXAMPLE 10

Preparation of triazolyl-tetrazinyl-aminotriazine, diaminoguanidinium salt [Z=(H$_2$NNH)$_2$C(NH$_2$)]

Via Method B: The sodium salt hydrate and diaminoguanidinium hydrochloride were combined in equimolar amounts in water to give a precipitate of red crystals (71%), mp 196° C., dec. Recrystallization from water gave mp 199° C., dec. Analysis showed: $^1$H NMR (DMSO-$d_6$): 4.59 (s, 4H), 6.68 (s, 2H), 7.16 (s, 2H), 8.58 (s, 2H). $^{13}$C NMR (DMSO-$d_6$): 146.1, 151.7, 153.1, 159.7, 167.7. Anal. Calcd for $C_5H_{10}N_{14}$: C, 22.56; H, 3.79; N, 73.66. Found: C, 22.52; H, 3.89; N, 71.88.

EXAMPLE 11

Preparation of triazolyl-tetrazinyl-aminotriazine, guanidinium salt [Z=C(NH$_2$)$_3$]

Via Method B: The sodium salt hydrate and guanidinium hydrochloride were combined in equimolar amounts in water to give a precipitate of red crystals (73%), mp 263° C., dec. Analysis showed: $^1$H NMR (DMSO-$d_6$): 6.69 (s, 2H), 6.95(s, 6H). $^{13}$C NMR (DMSO-d$_6$): 146.1, 151.7, 153.1, 157.6, 167.7. Anal. Calcd for C$_5$H$_8$N$_{12}$ (H$_2$O): C, 23.62; H, 3.96; N, 66.12. Found: C, 23.53; H, 3.96; N, 64.12.

EXAMPLE 12

Preparation of triazolyl-tetrazinyl-aminotriazine, methyltriphenylphosphonium salt [Z=CH$_3$P(C$_6$H$_5$)$_3$]

Via Method B: The sodium salt hydrate and methyltriphenylphosphonium bromide were combined in equimolar amounts in water to give a precipitate of red crystals, mp 69–72° C. Analysis showed: $^1$H NMR (DMSO-d$_6$): 3.10, 3.17 (pair of s, 3H), 6.66 (s, 2H), 7.72–7.88 (m, 15H). $^{13}$C NMR (DMSO-d$_6$): 118.9, 120.7, 129.9, 130.1, 133.0, 133.2, 134.86, 134.74, 146.1, 151.7, 153.1, 167.7.

EXAMPLE 13

Preparation of triazolyl-tetrazinyl-aminotriazine, triethylamine salt [Z=HN(C$_2$H$_5$)$_3$]

Via Method A: The parent acid was treated with an equimolar amount of triethylamine in methanol. The solvent was partially removed under reduced pressure to give red crystals, mp 205° C., dec. The product is the triethylamine salt, which has separated from solution in the form of a complex with an additional molecule of the parent acid. Analysis showed: $^1$H NMR (DMSO-d$_6$): 1.17 (t, 9H), 3.10 (q, 6H), 3.82 (very broad s), 7.33 (broad s, 3H). $^{13}$C NMR (DMSO-d$_6$): 8.4, 45.6, 145.1, 150.7, 151.4, 167.6. Anal. Calcd for C$_{10}$H$_{18}$N$_{10}$ (C$_4$H$_3$N$_9$): C, 36.92; H, 4.65; N, 58.43. Found: C, 36.54; H, 4.73; N, 57.56.

EXAMPLE 14

Preparation of triazolyl-tetrazinyl-aminotriazine, cobalt salt [cation =Co(II)]

Via Method B: The sodium salt hydrate and a water soluble cobalt (II) salt (e.g. cobalt (II) perchlorate hexahydrate or cobalt (II) nitrate hexahydrate) are combined in water to give a precipitate of red-orange crystals [Co(C$_4$H$_2$N$_9$)$_2$ (6H$_2$O)](89%). Analysis showed: Anal. Calcd for C$_8$H$_4$N$_{18}$Co (6H$_2$O): C, 18.50; H, 3.11; N, 48.55; Co, 11.35. Found: C, 18.45; H, 3.22; N, 48.24; Co, 11.27.

EXAMPLE 15

Preparation of triazolyl-tetrazinyl-aminotriazine, copper salt [cation =Cu(II)]

Via Method B: The sodium salt hydrate and a water soluble copper (H) salt (e.g. copper (II) perchlorate hexahydrate or copper (II) nitrate hemipentahydrate) are combined in water to give a precipitate of red-orange crystals [Cu(C$_4$H$_2$N$_9$)$_2$(5H$_2$O)](92%). Anal. Caled for C$_8$H$_4$N$_{18}$Cu (5H$_2$O): C, 18.99; H, 2.79; N, 49.84; Cu, 12.56. Found: C, 18.9; H 2.84; N, 49.48; Cu, 12.88.

EXAMPLE 16

Preparation of triazolyl-tetrazinyl-aminotriazine, aluminum salt [cation =Al(III)]

Via Method B: The sodium salt hydrate and a water soluble aluminum (III) salt (e.g. aluminum (III) perchlorate nonahydrate or aluminum (III) nitrate nonahydrate) are combined in water to give a precipitate of orange crystals [Al(C$_4$H$_2$N$_9$)$_3$(7.5H$_2$O)](78%). Analysis showed: $^1$H NMR (DMSO-d$_6$): 7.61, 7.68 (d). $^{13}$C NMR (DMSO-d$_6$): 144.5, 150.2, 150.5, 167.6.. Anal. Calcd for C$_{12}$H$_6$N$_{27}$Al(7.5H$_2$O): C, 20.87; H, 3.07; N, 54.77; Al, 3.91. Found: C, 21.24; H, 3.23; N, 54.53; Al, 3.38.

EXAMPLE 17

Preparation of triazolyl-tetrazinyl-aminotriazine, nickel salt [cation =Ni(II)]

Via Method B: The sodium salt hydrate and a water soluble nickel (II) salt (e.g. nickel (II) perchlorate hexahydrate or nickel (II) nitrate hexahydrate) are combined in water to give a precipitate of orange crystals [Ni(C$_4$H$_2$N$_9$)$_2$(xH$_2$O)](92% for x=6). Anal. Calcd for C$_8$H$_4$N$_{18}$Ni (6H$_2$O): C, 18.51; H, 3.11; N, 48.57; Ni, 11.31. Found: C, 18.57; H, 2.82, H, 47.85; Ni, 11.87.

EXAMPLE 18

Preparation of triazolyl-tetrazinyl-aminotriazine, barium salt [cation =Ba(II)]

Via Method B: The sodium salt hydrate and a water soluble barium (II) salt (e.g. barium (II) perchlorate xH$_2$O or barium (II) nitrate) are combined in water to give a precipitate of red crystals [Ba(C$_4$H$_2$N$_9$)$_2$(xH$_2$O)](87% for x=6). Analysis showed: $^1$H NMR (DMSO-d$_6$): 6.66 (s). $^{13}$C NMR (DMSO-d$_6$): 146.1, 151.8, 153.2, 167.7. For [Ba(C$_4$H$_2$N$_9$)$_2$(7H$_2$O)](85%); analysis showed $^1$H NMR (DMSO-d$_6$): 6.66 (s). $^{13}$C NMR (DMSO-d$_6$): 146.1, 151.8, 153.2, 167.7. Anal. Calcd for C$_8$H$_4$N$_{18}$Ba (7H$_2$O): C, 15.60; H, 2.95; N, 40.95; Ba, 22.31. Found: C, 15.22; H, 3.13; N, 39.14; Ba, 22.16.

A sample of the red crystals [Ba(C$_4$H$_2$N$_9$)$_2$(7H$_2$O)]was dried at 100° C. for 43 hours. Elemental analysis showed the crystals had lost water to yield [Ba(C$_4$H$_2$N$_9$)$_2$(2H$_2$O)]. Anal. Calcd for C$_8$H$_4$N$_{18}$Ba (2H$_2$O): C, 18.28; H, 1.53; N, 47.97; Ba, 26.13. Found: C, 18.41; H, 1.92; N, 46.31; Ba, 25.68.

EXAMPLE 19

Preparation of triazolo-tetrazino-aminotriazine, 3,6-dihydrazino-1,2,4,5-tetrazine salt [Z=H$_2$NNH(C$_2$N$_4$)NHNH$_3$]

Via Method A: The parent acid was stirred in methanol/water with an equimolar amount of 3,6-dihydrazino-1,2,4,5-tetrazine (DHT) for 5 hours. The mixture was filtered to remove the rust colored solid, mp 165° C., very rapid dec. [For comparison, the dec. points of DHT and the parent acid are 155° C. and 215° C., respectively]. $^1$H NMR (DMSO-d$_6$): 3.0–7.0 (various broad absorptions), 7.76, 7.69 (d), 8.52 (s). $^{13}$C NMR (DMSO-d$_6$): 144.4, 149.7, 150.6 (broadened), 162.4, 163.2, 167.7. For comparison spectra, DHT shows $^1$H NMR (DMSO-d$_6$): 4.25 (s, 4H), 8.38 (s, 2H)) and $^{13}$C NMR (DMSO-d$_6$): 163.3. The NMR spectra of the parent acid are given in example 4 above. The salt (19A) or complex (19B) may form.

EXAMPLE 20

Preparation of triazolo-tetrazino-aminotriazine, magnesium salt [cation =Mg(II)]

Via Method B: The sodium salt hydrate and a water soluble magnesium (II) salt (e.g. magnesium (II) perchlorate hexahydrate) are combined in water to give a precipitate of red crystals [Mg(C$_4$H$_2$N$_9$)$_2$(6H$_2$O)](96%). Anal. Calcd for $C_8H_4N_{18}Mg$ (6H$_2$O): C, 19.83; H, 3.33; N, 52.02; Mg, 5.01. Found: C, 19.85; H, 3.44; N, 51.72; Mg, 5.15. $^1$H NMR (DMSO-d$_6$): 6.66 (s). $^{13}$C NMR (DMSO-d$_6$): 146.1, 151.8, 153.2, 167.7.

EXAMPLE 21

Preparation of triazolo-tetrazino-aminotriazine, strontium salt [cation =Sr(II)]

Via Method B: The sodium salt hydrate and a water soluble strontium (II) salt (e.g. strontium (II) nitrate) are combined in water to give a precipitate of red-orange crystals [Sr(C$_4$H$_2$N$_9$)$_2$(8H$_2$O)](83%). Anal. Calcd for $C_8H_4N_{18}Sr$ (8H$_2$O): C, 16.45; H, 3.45; H, 43.17; Sr, 15.00. Found: C, 16.18; H, 3.65; N, 41.84; Sr, 14.79. $^1$H NMR (DMSO-d$_6$): 6.65 (s). $^{13}$CNMR(DMSO-d$_6$): 146.1, 151.8, 153.2, 167.7.

EXAMPLE 22

Preparation of triazolo-tetrazino-aminotriazine, potassium salt [Cation =K]

Via Method A: A suspension of the parent acid in water was well-stirred while a dilute aqueous solution containing an equivalent amount of potassium hydroxide (85% KOH) was added dropwise. The solution was filtered and the volatiles were removed from the filtrate under reduced pressure. The residue was washed with acetone and re-crystallized by dissolving in a minimum amount of water and adding acetone. The red crystals weighed 0.34 g after air-drying. The sample was then dried in a vacuum desiccator over Drierite for 24 hours to give 0.27 g [KC$_4$H$_2$N$_9$] (82%). Anal. Calcd for C$_4$H$_2$N$_9$K: C, 22.32; H, 0.94; N, 58.57; K, 18.17. Found: C, 21.94; H, 1.22; N, 56.61; K, 17.18. $^1$H NMR (DMSO-d$_6$): 6.66 (s). $^{13}$C NMR (DMSO-d$_6$): 146.1, 151.8, 153.2, 167.7.

The triazolyl-tetrazinyl-aminotriazine compounds of the pyrotechnic compositions of the present invention are high-nitrogen heterocyclic compounds that are particularly useful energetic ingredients for pyrotechnics because of their thermal stability, insensitivity, and their capability to moderate flame temperatures and propellant bum rates. They also provide efficient heating of the colorant metal cation, since it is part of the crystal structure of the high-energy, high-nitrogen compound. The triazolyl-tetrazinyl-aminotriazine compounds also provide a platform for a very large number of specialized salts useful in the pyrotechnic field, including those of metals, amines, or other cations. The pyrotechnic compositions of the present invention can be arranged into any appropriate fireworks display as determinable by those skilled in the art in light of the disclosure herein. Typical fireworks configuration include roman candle, single or multiple shells, bursts or flares and other such effects as are commonly used in the fireworks industry. These fireworks may be stationary or catapulted into the air, such as by use of a lifting charge, and include other necessary pyrotechnic components, including for example, colorants, oxidizer, black powder, bursting charge and other secondary charges, and fusing. It is particularly preferred that the pyrotechnic compositions of the present invention produce a minimal amount of smoke as to be useful not only in outdoor fireworks displays, but also useful in enclosed or confined arenas, such as staged productions providing one or more visual points of reference for an audience, indoors including stadium use, or otherwise within confirmed or limited spaces such as for use in the production of special effects for the film industry.

Preparation of colorants are exemplified below:

EXAMPLE 23

Preparation of azo(triazolodiaminotriazine)

Method C: A mixture of 0.30 g (1.8 mmol) of finely ground 1,2,4-triazolo[4,3-a][1,3,5]triazine-3,5,7-triamine in 35 ml of water was stirred vigorously at 25° C. during the addition of 0.60 g (7.2 mmol) of sodium bicarbonate and 0.90 g (3.6 mmol) of iodine. The mixture rapidly turned deep purple in color. Stirring was continued for 90 hours before the insoluble dark purple solid was removed by filtration, washed with water and dried to give (0.22 g, 71%). $^1$H NMR (D$_2$SO$_4$): 10.2 (s); $^{13}$C NMR (D$_2$SO$_4$): 139.2, 141.7, 142,6, 146.2.

Method D: A beaker containing a solution of 120 mg (0.72 mmol) of 1,2,4-triazolo[4,3-a][1,3,5]triazine-3,5,7-triamine and 360 mg (4.3 mmol) of sodium bicarbonate in 1 liter of water was placed in a closed container with iodine crystals (1.4 g). After 48 hours, sufficient iodine had sublimed and was absorbed by the water to produce 70 mg (56%) of dark purple solid precipitate. Anal. Calcd for C$_8$H$_8$N$_{16}$ (H$_2$O): C, 27.75; H, 2.91; N, 64.72. Found: C, 27.47; H, 3.00; N, 62.65.

The foregoing summary, description, and examples of the invention are not intended to be limiting, but are only exemplary of the inventive features which are defined in the claims.

What is claimed is:

1. A compound having the chemical formula:

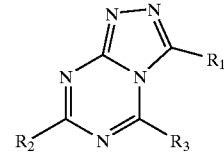

wherein R$_1$ is —NH$_2$, and R$_2$ and R$_3$ are independently electron donating groups.

2. The compound of claim 1, wherein R$_2$ and R$_3$ independently comprise electron donating groups selected from the group consisting of lower alkylamino, diloweralkylamino, amino, halo, aryl, lower alkoxy, lower aralkoxy, aryloxy, mercapto, and lower alkylthio.

3. The compound of claim 1, wherein R$_2$ and R$_3$ independently comprise electron donating groups selected from the group consisting of a hydroxyl salt, a carboxyl salt, —OR$_\alpha$, —CR$_{\alpha 3}$, —OCOR$_\alpha$, —NR$_{\alpha 2}$, and SR$_\alpha$, where R$_\alpha$ group is an alkyl group or.

4. The compound of claim 1, wherein R$_2$ and R$_3$ independently comprise electron donating groups selected from the group consisting of amino, hydroxy, lower alkoxy, lower alkylamino and diloweralkylamino.

5. The compound of claim of claim 1, wherein either R$_2$ or R$_3$ comprise —NH$_2$.

6. The compound of claim 1, wherein both R$_2$ and R$_3$ comprise —NH$_2$.

7. The compound of claim 1, wherein either R$_2$ or R$_3$ comprise —OCH$_3$.

8. The compound of claim 1, wherein both R$_2$ and R$_3$ comprise —OCH$_3$.

9. 1,2,4-triazolo[4,3-a][1,3,5]triazine-3,5,7-triamine.

10. A compound comprising separate final product formed from diazotizing the compound of claim 1.

11. The compound of claim 10, wherein the separate final product comprises the chemical structure of:

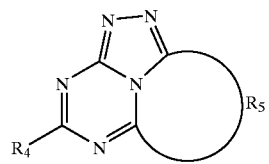

wherein R$_4$ is an electron donating group, and R$_5$ comprises a third fused ring having greater than five atoms comprising carbon atoms, nitrogen atoms, or a combination thereof.

12. The compound of claim 10, wherein the separate final product comprises chemical compositions for use in a field selected from the group consisting of pharmaceutical, energetic material, colorant, functional fluid, agricultural composition, ultraviolet stabilizer and ultraviolet absorber.

13. The compound of claim 12, wherein the separate final product comprises an energetic material selected from the group consisting of explosive, gas generator, and pyrotechnic.

14. The compound of claim 12, wherein the separate final product comprises an agricultural composition selected from the group consisting of herbicides, pesticides, fungicides and fertilizers.

15. The compound of claim 12, wherein the separate final product comprises a functional fluid.

16. The compound of claim 12, wherein the separate final product comprises a colorant selected from the group consisting of dyes, pigments and indicators.

17. The compound of claim 12, wherein the separate final product comprises a pharmaceutical.

18. A process for the preparation of 1,2,4-triazolo[4,3-a][1,3,5]triazine-3,5,7-substituted, acid salt, comprising the steps of:
dissolving a 2,4-substituted-6-hydrazino-s-triazine with an acid; and,
mixing the dissolved 2,4-substituted-6-hydrazino-s-triazine with a reagent of the formula RCN, wherein R comprises a leaving group, wherein the 2,4-substituted component of the 2,4-substituted-6-hydrazino-s-triazine independently comprise electron donating groups.

19. A process for the preparation of 1,2,4-triazolo[4,3-a][1,3,5]triazine-3,5,7-substituted compound, comprising the steps of:
dissolving a 2,4-substituted-6-hydrazino-s-triazine with an acid;
mixing the dissolved 2,4-substituted-6-hydrazino-s-triazine with a reagent of the formula RCN, wherein R comprises a leaving group;
removing acid salt crystals; and,
neutralizing the acid salt crystals by mixing with a substance more basic than 1,2,4-triazolo[4,3-a][1,3,5]triazine-3,5,7-substituted compound, wherein the 2,4-substituted component of the 2,4-substituted-6-hydrazino-s-triazine independently comprise electron donating groups.

20. The process of claim 18, wherein the electron donating groups independently are selected from the group consisting of a hydroxyl salt, carboxyl salt, —OR$_\alpha$, —OCR$_3$, —CR$_\alpha$R$_\beta$R$_\gamma$, —OCOR$_\alpha$, —NR$_\alpha$R$_\beta$, and SR$_\alpha$, where R$_\alpha$, R$_\beta$, and R$_\gamma$ groups are independently an alkyl group or H.

* * * * *